(12) United States Patent
De Jong et al.

(10) Patent No.: US 7,619,129 B2
(45) Date of Patent: Nov. 17, 2009

(54) PROCESS FOR THE SEPARATION OF OLEFINS AND PARAFFINS

(75) Inventors: Feike De Jong, Amsterdam (NL); Jan De With, Amsterdam (NL)

(73) Assignee: Shell Oil Company, Houston, TX (US)

( * ) Notice: Subject to any disclaimer, the term of this patent is extended or adjusted under 35 U.S.C. 154(b) by 721 days.

(21) Appl. No.: 11/017,491

(22) Filed: Dec. 20, 2004

(65) Prior Publication Data

US 2005/0154247 A1    Jul. 14, 2005

(30) Foreign Application Priority Data

Dec. 22, 2003    (EP)    ................................. 03258133

(51) Int. Cl.
*C07C 7/144*    (2006.01)
(52) U.S. Cl. ..................................... 585/818
(58) Field of Classification Search .................. None
See application file for complete search history.

(56) References Cited

U.S. PATENT DOCUMENTS

| 5,135,547 | A | * | 8/1992 | Tsou et al. | ...................... 95/44 |
| 6,339,182 | B1 | | 1/2002 | Muson et al. | ............... 585/809 |
| 6,579,343 | B2 | | 6/2003 | Brennecke et al. | ............. 95/51 |
| 6,623,659 | B2 | | 9/2003 | Munson et al. | ............. 252/184 |

FOREIGN PATENT DOCUMENTS

| DE | 19929482 | 3/2001 |
| EP | 311903 | 4/1989 |
| EP | 458598 | 11/1991 |
| GB | 2169301 | 7/1986 |
| WO | 01/40150 | 6/2001 |
| WO | WO0247802 | 6/2002 |
| WO | 02/078821 | 10/2002 |

OTHER PUBLICATIONS

Chem. Commun. 2000 195-196.
Angew. Chem. Int. Ed. 2002 41, No. 15 pp. 2771-2773.
Chem. Evr. J., 2002, 8, No. 17 pp. 3865-3871.
De Jong, F.; Visser, H.C. in Comprehensive Supramolecular Chemistry, eds. Atwood, J.L.; Davies, J.E.D.; MacNicol, D.D.; Vogtle, F.; Lehn, J-M.; Reinhoudt, D.N. Elsevier Science, Oxford, 1996, vol. 10, Chapter 2, p. 13-46.
Branco et al., "Highly selective transport of organic compounds by using supported liquid membranes based on ionic liquids" Angewandte Chemie. International Edition, vol. 41, No. 15, 2002, pp. 2771-2773, XP002326750.
Branco et al., "Studies on the selective tansport of organic compounds by using ionic liquids as novel supported liquid membranes" Chemistry—A European Journal, vol. 8, No. 17, 2002, pp. 3865-3871, XP002326751.
*J Mater Chem. Rev. 99*, 1999 2071-2084—Thomas Welton, Room-Temperature Ionic Liquids. Solvents for Synthesis and Catalysis, Chem. Rev. 1999, 99, pp. 2071-2083.

(Continued)

*Primary Examiner*—Tam M Nguyen (57) ABSTRACT

A process for the separation of olefinic hydrocarbons from a liquid feedstock composition comprising at least one olefinic hydrocarbon and at least one paraffinic hydrocarbon, said process comprising contacting the liquid feedstock with a supported ionic liquid membrane wherein the supported ionic liquid membrane comprises a membrane impregnated with an ionic liquid composition.

23 Claims, 1 Drawing Sheet

OTHER PUBLICATIONS

*Chem 8*, 1998 2627-2636—Charles M. Gordon, John D. Holbrey, Alan R. Kennedy and Kenneth R. Seddon, "Ionic liquid crystals: hexafluorophosphate salts," J. Mater. Chem. 1998, 8, pp. 2627-2636.

*Chem. Commun.* 2000 1261-1262—Hoon Sik Kim, Jae Hee Ryu, Honggon Kim, Byoung Sung Ahn and Yong Soo Kang, "Reversible olefin complexation by silver ions in dry poly(vinyl methyl ketone) membrane and its application to olefin/paraffin separations," Chem. Commun. 200, pp. 1261-1262.

*Chem. Commun.* 2000 195-196—Young Hee Kim, Jae Hee Ryu, Jin Yong Bae, Yong Soo Kang, and Hoon Sik Kim, "Reactive polymer membranes containing cuprous complexes in olefin/paraffin separation," Chem. Commun., 2000, pp. 195-196.

*Angew. Chem. Int.* Ed. 2002 41, No. 15 pp. 2771-2773—Luis C. Branco, Joao G. Crespo, and Carlos A. M. Afonso, "Highly Selective Transport of Organic Compounds by Using Supported Liquid Membranes Based on Ionic Liquids," Angew. Chem. Int. Ed. 2002, 41, No. 15, pp. 2771-2773.

*Chem. Evr. J.*, 2002, 8, No. 17 pp. 3865-3871—Luis C. Branco, Joao G. Crespo, and Carlos A. M. Afonso, "Studies on the Selective Transport of Organic Compounds by Using Ionic Liquids as Novel Supported Liquid Membranes," Chem. Eur. J. 2002, 8, No. 17, pp. 3865-3871.

*J Chem. Tech. Biotech.* 68, 1997 351-356—Kenneth R. Seddon, "Ionic Liquids for Clean Technology," J. Chem. Tech. Biotechnol. 0268-2575/97, pp. 351-356.

*J. Phys. Condensed Matter.* vol. 5 (Supp 34B) 1993 B99-B106—John E. Enderby, "Ionic liquids: recent progress and remaining problems," J. Phys.: Condens. Matter 5 (1993) pp. B99-B106.

*Chem & Eng. News,* Mar. 30, 1998 32-37—Michael Freemantle, "Designer Solvents," Chemical and Engineering News, Mar. 30, 1998, pp. 32-37.

De Jong, F.; Visser, H.C. in Comprehensive Supramolecular Chemistry, eds. Atwood, J.L.; Davies, J.E.D.; MacNicol, D.D.; Vogtle, F.; Lehn, J-M.; Reinhoudt, D.N. Elsevier Science, Oxford, 1996, vol. 10, Chapter 2, pp. 13-46.

* cited by examiner

FIG. 1

PROCESS FOR THE SEPARATION OF OLEFINS AND PARAFFINS

FIELD OF THE INVENTION

The present invention relates to the separation of olefinic hydrocarbons from a liquid feedstock composition comprising at least one olefinic hydrocarbon and at least one paraffinic hydrocarbon.

BACKGROUND OF THE INVENTION

Olefinic hydrocarbons are frequently used in many industrial applications, including the manufacture of polymers such as polyethylene, as drilling mud additives, and as intermediates for the production of detergents. There exist many industrial processes for the manufacture of olefins. However, many of these processes produce hydrocarbon streams that are mixtures of olefinic hydrocarbons, paraffinic hydrocarbons and often other impurities such as oxygenates and aromatics.

One such process for the production of olefins is the partial dehydrogenation of paraffinic hydrocarbons, which produces olefinic hydrocarbons and some unreacted paraffinic hydrocarbons. Another such process is the dehydration of alcohols, which produces an olefinic hydrocarbon composition as well as paraffinic hydrocarbons and unreacted alcohol feedstock.

A further industrial process which may be used for the manufacture of olefins is the so-called Fischer-Tropsch (FT) hydrocarbon synthesis process. The feedstock for this process is syngas, a mixture of carbon monoxide and hydrogen, which is generally inexpensive and can be readily derived from natural gas, coal, coke, and other carbonaceous compounds.

Unfortunately, however, the FT process is not always selective towards the production of olefins. The product stream derived from the Fischer-Tropsch process typically contains a mixture of olefins, saturated hydrocarbons, aromatics and oxygenates. While reaction conditions and catalysts can be tuned to manufacture streams rich in a desired species (e.g. olefinic hydrocarbons), the FT product stream can also contain a significant percentage of the other types of compounds produced by the FT process (e.g. paraffinic hydrocarbons).

Clearly, olefinic hydrocarbon compositions produced from the processes mentioned hereinabove should be purified, by separation of the desired olefinic products from the other products produced, before they are sold commercially. However, conventional distillation techniques are frequently inadequate to separate olefinic hydrocarbons and paraffinic hydrocarbons which have similar molecular weights since they frequently have closely related boiling points.

Various processes for separating olefinic hydrocarbons from paraffinic hydrocarbons are taught in the prior art. One such process involves the use of an ionic liquid composition comprising a metal salt dissolved or dispersed in the ionic liquid solution for the separation of olefinic hydrocarbons from paraffinic hydrocarbons wherein the metal salt/ionic liquid forms a complex with the olefinic hydrocarbon. The separation process can be described by the following general scheme: firstly, a two-phase composition of the olefin/paraffin composition and the metal salt/ionic liquid composition is formed; secondly, the olefins are absorbed and complexed with the metal salt/ionic liquid composition; thirdly, the resultant paraffinic composition is separated from the metal salt/ionic liquid composition; and finally, the olefins are isolated from the metal salt/ionic liquid composition by desorption at increased temperature and/or reduced pressure.

The use of membranes for the separation of olefinic hydrocarbons from paraffinic hydrocarbons has been achieved with varying degrees of success. However, membrane separation processes have only regularly been reported for the purification of gaseous olefinic hydrocarbon feedstocks having a narrow distribution of carbon numbers, typically a single carbon number, e.g. $C_2$ or $C_3$.

Despite there being processes available for separating liquid olefinic hydrocarbons and liquid paraffinic hydrocarbons, there is still a need to provide an improved process for the separation of olefinic hydrocarbons from paraffinic hydrocarbons. In particular, there is a need to provide a process which will not only provide olefinic compositions of sufficient purity to be commercially useful but which will also be highly energy efficient. It would also be desirable to provide a process which is capable of separating olefinic hydrocarbons from paraffinic hydrocarbons in a liquid feedstock composition having a broad spectrum of average carbon numbers (e.g. $C_5$-$C_{40}$)

SUMMARY OF THE INVENTION

It has now surprisingly been found that olefinic hydrocarbons can be separated from paraffinic hydrocarbons in a liquid feedstock containing liquid olefinic hydrocarbons and liquid paraffinic hydrocarbons by the use of a supported liquid membrane based upon a membrane which has been impregnated with an ionic liquid composition. It has also been surprisingly found that this supported ionic liquid membrane separation processes can be carried out in the liquid phase with no loss of the membrane solution into either the feedstock composition or the olefinic hydrocarbon product composition.

Thus, the present invention relates to a process for the separation of olefinic hydrocarbons from a liquid feedstock composition comprising at least one olefinic hydrocarbon and at least one paraffinic hydrocarbon, said process comprising contacting the liquid feedstock with a supported ionic liquid membrane wherein the supported ionic liquid membrane comprises a membrane impregnated with an ionic liquid composition. Since the separation of olefinic hydrocarbons from paraffinic hydrocarbons using supported ionic liquid membranes can operate under ambient conditions, the process is highly energy efficient and produces very little waste product.

BRIEF DESCRIPTION OF THE DRAWING

A schematic diagram of the glass transport cell is given in FIG. 1.

DETAILED DESCRIPTION OF THE INVENTION

The term "hydrocarbon" as used herein, relates to a compound in which the dominant constituent elements are carbon and hydrogen. The term "paraffinic hydrocarbon" as used herein, refers to a hydrocarbon compound wherein all carbon-carbon bonds are fully saturated. The term "olefinic hydrocarbon" as used herein, refers to a hydrocarbon compound wherein at least one carbon-carbon bond is a carbon-carbon double bond.

The process of the present invention produces an "olefinic hydrocarbon product composition" which comprises the olefinic hydrocarbon(s) which has been separated from the feedstock composition by the process of the present invention.

The feedstock composition used in the process of the present invention is a liquid hydrocarbon composition comprising at least one olefinic hydrocarbon and at least one paraffinic hydrocarbon. A solvent may optionally be incorporated into the feedstock composition. It is preferred that the feedstock composition does not comprise an added solvent.

The feedstock composition as used herein must be liquid at the operating temperature and pressure of the separation process of the present invention. The separation process of the present invention may be carried out at room temperature (25° C.) and at atmospheric pressure (1 atm).

The olefinic hydrocarbons present in the feedstock composition are preferably $C_5$-$C_{40}$ olefinic hydrocarbons, more preferably $C_6$-$C_{18}$ olefinic hydrocarbons. The olefinic hydrocarbons used herein are even more preferably olefins in the detergent range ($C_8$-$C_{16}$). The olefinic hydrocarbons present in the feedstock composition may contain more than one olefinic bond. Preferably the olefinic hydrocarbons in the feedstock composition of the process of the present invention are mono-olefinic hydrocarbons.

The olefinic hydrocarbons present in the feedstock composition are preferably selected from linear or branched internal-olefins, linear or branched alpha-olefins, ($C_1$-$C_4$ alkyl-) substituted or unsubstituted cyclic olefins, and mixtures thereof. More preferably the olefinic hydrocarbons present in the feedstock composition are selected from linear or branched alpha-olefins, linear or branched internal-olefins and mixtures thereof.

The olefinic hydrocarbons present in the feedstock composition may optionally contain one or more functional groups, provided that the functional groups do not react with the ionic liquid composition or the membrane used in the process of the present invention. Preferably the olefinic hydrocarbons present in the feedstock composition do not contain any functional groups. The olefinic hydrocarbons may also contain a heteroatom (i.e. an atom other than carbon) in the hydrocarbon chain. Examples of suitable heteroatoms include oxygen, nitrogen, sulfur and phosphorus. Preferably, however, the hydrocarbon chain does not contain any heteroatoms.

The paraffinic hydrocarbons present in the feedstock composition are preferably $C_5$-$C_{40}$ paraffinic hydrocarbons, more preferably $C_6$-$C_{18}$ paraffinic hydrocarbons, especially $C_8$-$C_{16}$ paraffinic hydrocarbons.

The paraffinic hydrocarbons present in the feedstock composition are preferably selected from linear or branched non-cyclic paraffins, ($C_1$-$C_4$ alkyl-) substituted or unsubstituted cyclic paraffins, ($C_1$-$C_4$ alkyl-) substituted or unsubstituted polycyclic paraffins and mixtures thereof. More preferably the paraffinic hydrocarbons present in the feedstock composition are selected from linear paraffins, branched paraffins and mixtures thereof.

Other compounds may optionally be present in the feedstock composition. Typically, these include aromatics, oxygenates, and sulfur, nitrogen and phosphorous containing hydrocarbons. The type of these optional compounds will depend on the origin of the feedstock composition, e.g. Fischer-Tropsch or otherwise.

The feedstock composition may be derived from any industrial process which produces a mixture of olefinic hydrocarbons and paraffinic hydrocarbons. In a preferred embodiment, the feedstock composition is derived from a Fischer-Tropsch process.

The "Fischer-Tropsch" hydrocarbon synthesis involves the reaction of carbon monoxide and hydrogen ("synthesis gas") in the presence of a Fisher-Tropsch catalyst, e.g. a cobalt or iron based Fischer-Tropsch catalyst, to produce hydrocarbons. The synthesis gas used in the Fischer-Tropsch hydrocarbon synthesis is derived from cheap, abundantly available natural gas or coal.

Typically, Fischer-Tropsch processes produce a hydrocarbon product stream comprising paraffinic hydrocarbons, olefinic hydrocarbons (including internal- and alpha-olefins), aromatics, and oxygenates (commonly alcohols, but may also include ethers, esters, acids, aldehydes, acid anhydrides, and ketones).

The process of the present invention comprises contacting the feedstock composition described hereinabove with a supported ionic liquid membrane. The supported ionic liquid membrane comprises a membrane impregnated with an ionic liquid composition.

Supported ionic liquid membranes are generally prepared by the immersion of a suitable membrane in an ionic liquid composition, such that substantially all of the pores are filled with the ionic liquid composition. Optionally, the membrane may be immersed in the ionic liquid composition under vacuum. In this context, the term "substantially all" means that preferably 95% or more of the pores of the membrane are filled with the ionic liquid composition, more preferably 99% or more, especially 100% of the pores of the membrane are filled with the ionic liquid composition. The membrane is then removed from the ionic liquid composition, and any excess surface liquid is removed. The ionic liquid composition is drawn into and held within the pores of the membrane by capillary forces.

Any type of membrane suitable for use with an ionic liquid composition may be used in the process of the present invention to form the supported ionic liquid membrane. The material of the membrane is not critical. However, the membrane should not be reactive with the ionic liquid composition or the feedstock and product compositions. The physical properties of the membrane which is to be impregnated with the ionic liquid composition are not critical as long as the capillary forces acting within the membrane pores are sufficiently high to prevent the ionic liquid composition leaching out into either the feedstock composition or the olefinic hydrocarbon product composition. The membrane used may be isotropic or anisotropic, hydrophilic or hydrophobic. However, the membrane should have an affinity for the ionic liquid composition which is to be immobilised within its pore structure. Preferably, the membrane is hydrophilic.

Suitable materials for the membrane are known to those skilled in the art in the field of membrane separation. Examples of types of suitable membranes include mesoporous and macroporous polymer membranes, ceramic membranes, zeolite membranes, and porous alumina and steel membranes. Preferably the membrane is a mesoporous or a macroporous polymer membrane.

The polymer material for use in the polymer membrane is not critical. Suitable polymer materials are known to those skilled in the art in the field of membrane separation. Examples of suitable materials for polymer membranes include: polysulfone; cellulose acetate; regenerated cellulose; polyamide; polycarbonates; polyimides; polyvinylidene fluoride; polyethersulfone; hydrophilic polypropylene; nylon; polyacrylate; polyetherimide; and non-hydrophilic polypropylene.

Preferably the membrane is a polyvinylidene fluoride, polyethersulfone, polyacrylate, polyetherimide, or a polycarbonate membrane.

The configuration of the membrane is not critical. The membrane may be of a flat sheet, tubular, spiral wound, or hollow fibre configuration.

The ionic liquid composition used in the process of the present invention preferably comprises one or more ionic liquids, wherein the one or more ionic liquids comprise a large organic cation with a weakly coordinating anion. The ionic liquids used herein are preferably room temperature ionic liquids.

Room temperature ionic liquids as used herein are organic salt compounds with very low melting points and are liquid at a temperature of 25° C. and a pressure of 1 atmosphere. Ionic liquids generally remain in the liquid phase over a wide temperature range. Ionic liquids also have essentially no vapour pressure and most ionic liquids are air and water stable at room temperature. Furthermore, certain ionic liquids are insoluble in water and in hydrocarbon solvents.

The properties of ionic liquids can be tailored according to their intended use. This can be achieved by varying the cation and anion of the ionic liquid compound. For examples of this see J. Chem. Tech. Biotechnol., 68, 1997, 351-356; J. Phys. Condensed Matter, 5 (Supp 34B), 1993, B99-B106; Chemical and Engineering News, Mar. 30, 1998, 32-37; J. Mater. Chem., 8, 1998, 2627-2636; and Chem. Rev., 99, 1999, 2071-2084, the contents of which are incorporated herein by reference.

Ionic liquids may be bought commercially or can be synthesised by techniques well known to those skilled in the art of synthetic chemistry. One type of ionic liquid may be formed by reacting a nitrogen-containing heterocyclic ring, preferably a heteroaromatic ring, with an alkylating agent (e.g. an alkyl halide). The resultant quaternary ammonium salt may subsequently be subjected to an ion exchange reaction, or other suitable reaction with various Lewis acids or their conjugate bases, thus forming an ionic liquid. Suitable heteroaromatic rings include optionally substituted pyridines, imidazoles, pyrroles, pyrrolidines, thiazoles, oxazoles, isooxazoles, and pyrazoles. These rings can be alkylated with virtually any linear, branched, or cyclic $C_1$-$C_{20}$ alkyl group, preferably $C_1$-$C_{16}$ alkyl groups since groups larger than this may form low melting solids as opposed to ionic liquids.

Various trialkylphosphines, thioethers, and cyclic and non-cyclic quaternary ammonium salts have also been used to form ionic liquids.

Ionic liquids can be neutral, Lewis-basic or Lewis-acidic. Neutral pH ionic liquids are preferable if it is desired not to isomerise the olefinic hydrocarbons which are to be separated. However, if it is not a concern whether the olefinic hydrocarbon composition is isomerised, i.e. if the olefinic hydrocarbons in the feedstock composition are already isomerised, or the focus of the separation is the removal of olefinic hydrocarbons from a paraffinic hydrocarbon stream, then Lewis-acidic ionic liquids can be employed.

Any weakly coordinating anion may be employed as the counterion in the ionic liquids herein. Suitable counterions for the ionic liquids herein include gallium tetrachloride, tetrafluoroborate, tetrachloroborate, hexafluorophosphate, tris(perfluoroalkyl)trifluorophosphate, nitrate, trifluoromethylsulfonate (triflate), methylsulfonate, methylsulfate, p-toluenesulfonate, octylsulfate, bis(trifluoromethylsulfonyl)imide, tris(trifluoromethylsulfonyl)methide, bis (trifluoromethyl)imide, hydrogensulfate, dicyanamide, bis (pentafluoroethylsulfonyl)imide, formate, acetate, (mono- or di-hydrogen)-phosphate, phosphate, trifluoroacetate, hexafluoroantimonate, hexafluoroarsenate, tetrachloroaluminate, tetrabromoaluminate, perchlorate, hydroxide anion, copper dichloride anion, iron trichloride anion, zinc trichloride anion, as well as various borate anions and various lanthanum, nickel, cobalt, manganese, and other metal containing anions.

The anion of the ionic liquid(s) for use herein is not critical provided that the anion used forms an ionic liquid with the cation employed. The preferred anions for use in the ionic liquids herein are selected from tetrachloroaluminate, tetrafluoroborate, hexafluorophosphate, nitrate, trifluoromethylsulfonate (triflate), methylsulfonate, methylsulfate, p-toluenesulfonate, bis(trifluoromethylsulfonyl)imide, hydrogensulfate, dicyanamide, (bis(pentafluoroethylsulfonyl)imide, acetate, (mono-or dihydrogen)-phosphate, phosphate, trifluoroacetate, copper dichloride anion, iron trichloride anion, and zinc trichloride anion.

More preferably, the anions of the ionic liquids of the process of the present invention are selected from bis(trifluoromethylsulfonyl)imide, tetrafluoroborate, nitrate, trifluoroacetate, methylsulfonate, trifluoromethylsulfonate, and dicyanamide.

Preferably, the ionic liquid comprises a nitrogen-containing heterocyclic cation. The nitrogen-containing heterocyclic cation may optionally be a nitrogen-containing heteropolycyclic cation or a heteropolyaromatic cation. Suitable nitrogen-containing heterocyclic cations include optionally substituted imidazolium, pyridinium, pyrrolinium, pyrrolidinium, thiazolium, quinolinium, oxazolium, isoxazolium, pyrazolium, piperidinium, morpholinium, pyrimidinium, pyrazinium, indolium, isoquinolinium, and cations of 1,4-diazabicyclo[2.2.2]octane, 1,8-diazabicyclo[5.4.0]undec-7-ene, and 1,5-diazabicyclo[4.3.0]non-5-ene. All of the above cations may be substituted with any linear, branched or cyclic $C_1$-$C_{20}$ alkyl group. More preferably the ionic liquid comprises a nitrogen-containing heteroaromatic cation. Most preferably, the cations used in the ionic liquids of the process of the present invention are optionally substituted imidazolium and pyridinium cations.

Preferred imidazolium cations for use herein are those having the formula (I) below:

(I)

wherein $R_1$, $R_2$ and $R_3$ are independently selected from hydrogen, $C_1$-$C_{20}$ alkyl groups, and $C_1$-$C_{20}$ alkoxyalkyl groups. In one preferred embodiment herein, $R_1$ and $R_3$ are independently selected from hydrogen and $C_1$-$C_{16}$ alkyl groups, more preferably hydrogen and $C_1$-$C_8$ alkyl groups. In another preferred embodiment herein, $R_1$ and $R_3$ are independently selected from hydrogen, methyl, ethyl, propyl, butyl, hexyl and octyl. In another preferred embodiment, $R_1$ is hydrogen or methyl and $R_3$ is selected from ethyl, propyl, butyl, hexyl and octyl. In another preferred embodiment herein, $R_2$ is hydrogen or methyl.

Preferred pyridinium cations for use herein are those having the formula (II) below:

(II)

wherein $R_4$ and $R_5$ are independently selected from hydrogen, $C_1$-$C_{20}$ alkyl groups, and $C_1$-$C_{20}$ alkoxyalkyl groups. In one preferred embodiment herein, $R_4$ and $R_5$ are independently selected from $C_1$-$C_{16}$ alkyl groups. In another preferred embodiment, $R_4$ and $R_5$ are independently selected from $C_1$-$C_8$ alkyl groups. In another preferred embodiment herein, $R_4$ and $R_5$ are independently selected from methyl, ethyl, propyl, butyl, hexyl, and octyl.

In one preferred embodiment, the cations of the ionic liquid for use herein are selected from the cations of 1-methyl-3-H-imidazolium, 1-ethyl-3-H-imidazolium, 1-propyl-3-H-imidazolium, 1-butyl-3-H-imidazolium, 1-hexyl-3-H-imidazolium, 1-octyl-3-H-imidazolium, 1-ethyl-3-methyl-imidazolium, 1-propyl-3-methyl-imidazolium, 1-butyl-3-methyl-imidazolium, 1-hexyl-3-methyl-imidazolium, 1-octyl-3-methyl-imidazolium, 1-ethyl-3-methyl-pyridinium, 1-propyl-3-methyl-pyridinium, 1-butyl-3-methyl-pyridinium, 1-hexyl-3-methyl-pyridinium, 1-octyl-3-methyl-pyridinium, 1-ethyl-4-methyl-pyridinium, 1-propyl-4-methyl-pyridinium, 1-butyl-4-methyl-pyridinium, 1-hexyl-4-methyl-pyridinium, and 1-octyl-4-methyl-pyridinium.

Preferred ionic liquids for use herein are selected from any combination of optionally substituted imidazolium or pyridinium cations having the formulae (I) or (II) above with any of the anions selected from tetrachloroaluminate, tetrafluoroborate, hexafluorophosphate, nitrate, trifluoromethylsulfonate (triflate), methylsulfonate, methylsulfate, p-toluenesulfonate, bis(trifluoromethylsulfonyl)imide, hydrogensulfate, dicyanamide, (bis(pentafluoroethylsulfonyl)imide, acetate, (mono-or dihydrogen)-phosphate, phosphate, trifluoroacetate, copper dichloride anion, iron trichloride anion, and zinc trichloride anion.

In a preferred embodiment, the ionic liquids for use herein are selected from a combination of an anion and a cation wherein the cation is selected from 1-methyl-3-H-imidazolium, 1-ethyl-3-H-imidazolium, 1-propyl-3-H-imidazolium, 1-butyl-3-H-imidazolium, 1-hexyl-3-H-imidazolium, 1-octyl-3-H-imidazolium, 1-ethyl-3-methyl-imidazolium, 1-propyl-3-methyl-imidazolium, 1-butyl-3-methyl-imidazolium, 1-hexyl-3-methyl-imidazolium, 1-octyl-3-methyl-imidazolium, 1-ethyl-3-methyl-pyridinium, 1-propyl-3-methyl-pyridinium, 1-butyl-3-methyl-pyridinium, 1-hexyl-3-methyl-pyridinium, 1-octyl-3-methyl-pyridinium, 1-ethyl-4-methyl-pyridinium, 1-propyl-4-methyl-pyridinium, 1-butyl-4-methyl-pyridinium, 1-hexyl-4-methyl-pyridinium or 1-octyl-4-methyl-pyridinium, and the anion is selected from bis(trifluoromethylsulfonyl)imide, tetrafluoroborate, nitrate, trifluoroacetate, methylsulfonate, trifluoromethylsulfonate, and dicyanamide.

A particularly preferred ionic liquid for use herein is selected from 1-butyl-3-methyl-imidazolium nitrate, 1-ethyl-3H-imidazolium nitrate, and 1-ethyl-3-methyl-imidazolium triflate.

Certain low melting solids can be used in place of room temperature ionic liquids, depending upon the particular separation to be effected. Low melting solids are generally very similar to ionic liquids, but they have melting points in the range from room temperature (25° C.) to 100° C. or are liquid under the conditions of the process of the present invention.

It has further been found that the introduction of metal salts capable of forming complexes with olefinic hydrocarbons increases the selectivity of the supported ionic liquid membrane in the separation of olefinic hydrocarbons from paraffinic hydrocarbons without the need for increased temperature and/or reduced pressure to facilitate separation of the olefinic hydrocarbons from the ionic liquid composition.

Hence, in one preferred embodiment herein, the ionic liquid composition comprises a metal salt dissolved, dispersed, or suspended in the ionic liquid composition.

The metal salt used herein should be capable of forming a complex with an olefinic hydrocarbon. Preferred metal salts for use herein are selected from the salts of silver, copper, manganese, zinc, platinum, palladium, nickel, cobalt, iron, gold, ruthenium, rhodium, chromium and molybdenum, and mixtures thereof.

The anion of the metal salts are known to those skilled in the art and some examples are provided below. Typical metal salts capable of forming a complex with an olefin include $AgCl$, $AgF$, $AgNO_3$, $AgCF_3SO_2NSO_2CF_3$, $AgCH_3SO_3$, $AgCF_3SO_3$, $AgBF_4$, $AgPF_6$, $AgClO_4$, $Ag(CF_3CO_2)$, $CuCl$, $CuBr$, $CuNO_3$, $Ni(BF_4)_2$, $Ni(CH_3CO_2)_2$, $Ni(NO_3)_2$, and $PtCl_2$. More preferably, the metal salts are silver or copper salts, especially silver salts. Particularly preferred metal salts for use herein are selected from $AgNO_3$, $AgCH_3SO_3$, $AgCF_3SO_3$, $AgCF_3SO_2NSO_2CF_3$, $AgBF_4$, $Ag(CF_3CO_2)$ $CuCl$, $CuNO_3$, $CuBr$ and mixtures thereof. In an especially preferred embodiment herein, the metal salt is $AgNO_3$.

Preferably, the ionic liquid composition used herein is non-aqueous, i.e. the ionic liquid composition comprises less than about 5%, preferably less than about 1%, especially 0%, by weight of water.

The process for the separation of olefinic hydrocarbons from a liquid feedstock composition comprising at least one olefinic hydrocarbon and at least one paraffinic hydrocarbon comprises contacting the liquid feedstock composition with a supported ionic liquid membrane under conditions suitable to selectively separate olefins from paraffins.

In particular, the process for the separation of olefinic hydrocarbons from a liquid feedstock composition comprising at least one olefinic hydrocarbon and at least one paraffinic hydrocarbon comprises contacting the liquid feedstock composition with a supported ionic liquid membrane under conditions suitable to selectively separate olefins from paraffins, wherein the olefinic hydrocarbons separated are collected in a receiving phase.

While not wishing to be bound by theory, it is believed that the process of the present invention occurs as follows. The olefinic hydrocarbons and paraffinic hydrocarbons present in the feedstock composition partition between the ionic liquid composition within the pores of the membrane and the feedstock composition. The olefinic hydrocarbons partitioned into the ionic liquid composition within the pores of the membrane form reversible complexes in equilibrium with the metal salt present in the ionic liquid composition. The olefinic hydrocarbons, paraffinic hydrocarbons and the reversible metal salt olefinic hydrocarbon complex diffuse to the permeate side of the supported ionic liquid membrane due to the concentration gradient within the supported ionic liquid membrane. The olefinic hydrocarbons and paraffinic hydrocarbons partition between the ionic liquid composition within the pores of the membrane and the receiving phase solvent, thus driving the equilibrium of the reversible metal salt olefinic hydrocarbon complex in favour of generating more non-complexed olefinic hydrocarbons in the ionic liquid composition at the permeate side of the supported ionic liquid membrane.

The conditions for the process of the present invention are not critical provided that the temperature and pressure are such that the ionic liquid composition is in the liquid phase when the process is carried out.

The temperature of the process of the present invention should be below the temperature at which the membrane becomes deformed and/or melted. The temperature for the process of the present invention should also be such that the feedstock composition is a liquid feedstock composition when the separation process is carried out. The temperature for the process of the present invention should preferably be such that the receiving phase is liquid when the separation process is carried out. The temperature used in the process of the present invention may be in the range from about −50° C. to about 300° C., preferably in the range from about 0° C. to about 200° C., and more preferably in the range from about 25° C. to about 150° C.

For economic and environmental reasons, it may be desirable to perform the process of the present invention at room temperature, or at the temperature at which the liquid feedstock composition emerges as a product stream from its process of manufacture (e.g. a Fischer-Tropsch product stream).

The pressure for the process of the present invention is not critical provided that the feedstock composition is a liquid feedstock composition at the pressure employed. The pressure for the process of the present invention may be in the range from about 1 bar to about 30 bar. A pressure difference may exist across the membrane, provided that the pressure difference is not so large that the ionic liquid composition is expelled from the pores of the membrane.

For economic and environmental reasons, it may be desirable to perform the process of the present invention at atmospheric pressure or at the pressure at which the liquid feedstock composition emerges as a product stream from its' process of manufacture.

The olefinic hydrocarbon product composition can be collected in a receiving phase by any technique known in the art. Preferably, the receiving phase of the process of the present invention is a solvent.

The receiving phase solvent is typically any suitable solvent which is inert to the olefinic hydrocarbon product composition and in which the olefinic hydrocarbon product composition is soluble. The receiving phase solvent should also be inert to the ionic liquid composition and is chosen such that the ionic liquid composition is not soluble in the receiving phase solvent. The olefinic hydrocarbon product composition may optionally be separated from the receiving phase solvent at the end of the process and before the olefinic hydrocarbon product composition is used as a feedstock for further reactions. The receiving phase solvent of the present invention may be chosen such that the boiling point(s) and melting point(s) of the solvent(s) and the separated olefinic hydrocarbon product composition(s) are sufficiently different that recovery of the olefinic hydrocarbon product may be performed by conventional separation techniques, e.g. distillation.

In one embodiment herein, the receiving phase solvent is a paraffinic hydrocarbon or an oxygenate. The receiving phase solvent may be selected from pentane, hexane, heptane, octane, decane, dodecane, tetradecane, diisobutyl carbinol, methyltertiarybutyl ether (MTBE) and diethyl ether.

The process of the present invention may be performed as a batch, semi-continuous or continuous phase operation. Preferably the process of the present invention is performed as a continuous phase operation.

The process of the present invention produces an olefinic hydrocarbon product composition and a retentate composition. As mentioned hereinabove, the olefinic hydrocarbon product composition comprises the olefinic hydrocarbon(s) which has been separated from the feedstock composition. The olefinic hydrocarbon product composition is enriched in olefinic hydrocarbons over the feedstock composition. The olefinic hydrocarbon product composition may also comprise small amounts of paraffinic hydrocarbons, excluding any paraffinic hydrocarbons present in the receiving phase solvent, which may be transferred concurrently with the olefinic hydrocarbons. Preferably, the amount of paraffinic hydrocarbons in the olefinic hydrocarbon product composition is less than about 20% wt., more preferably less than about 10% wt., especially less than about 5% wt., excluding any paraffinic hydrocarbons present in the receiving phase solvent.

The retentate composition is the stream which is left behind after the feedstock composition has been subjected to the process of the present invention and which contains the compounds which are not preferentially separated from the feedstock composition by the supported ionic liquid membrane used in the process of the present invention (e.g. paraffins). The retentate composition is enriched in paraffinic hydrocarbons over the feedstock composition. The retentate composition can also comprise olefinic hydrocarbons which have not passed through the supported ionic liquid membrane. Preferably, the amount of olefinic hydrocarbons present in the retentate composition is reduced by about 20% wt. or more, more preferably about 30% wt. or more, especially about 40% wt. or more relative to the initial amount of olefinic hydrocarbons in the feedstock composition.

The process of the present invention may also be used for the purification of a paraffinic hydrocarbon feedstock composition comprising at least one paraffinic hydrocarbon and at least one olefinic hydrocarbon impurity wherein the concentration of the olefinic hydrocarbon impurity in the retentate composition is reduced over the concentration of olefinic hydrocarbon impurity in the feedstock composition.

The separation process of the present invention can be repeated more than once on the feedstock composition and/or the olefinic hydrocarbon product composition in order to obtain the desired purity of the olefinic hydrocarbon product composition and/or the retentate composition.

The invention will be further illustrated by the following examples, however, without limiting the invention to these specific embodiments.

EXAMPLES

The examples described hereinbelow were all performed using a glass transport cell based upon the experimental set-up used in De Jong, F.; Visser, H. C. in *Comprehensive Supramolecular Chemistry*, eds. Atwood, J. L.; Davies, J. E. D.; MacNicol, D. D.; Vogtle, F.; Lehn, J.-M.; Reinhoudt, D. N. Elsevier Science, Oxford, 1996, vol. 10, Chapter 2, p. 13-46; which are all herein incorporated by reference. The glass transport cell of the examples is set up as follows.

Figure 1:
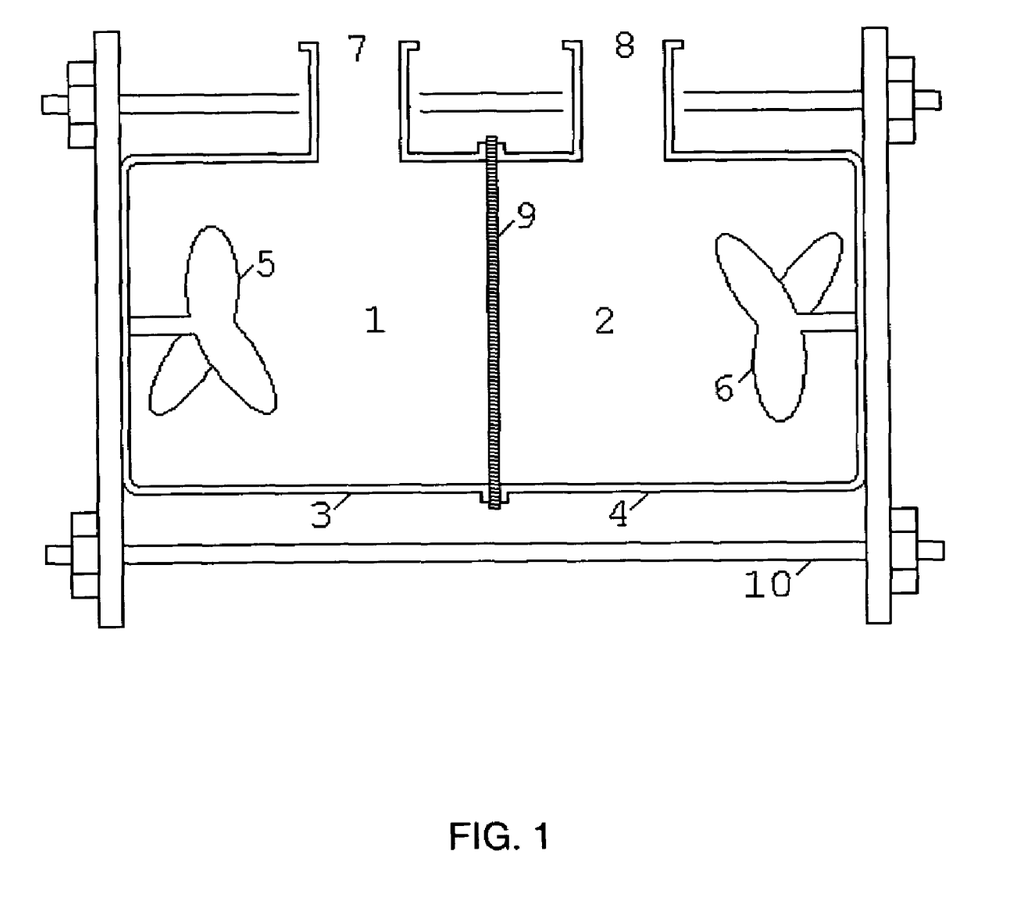

A schematic diagram of the glass transport cell is given in FIG. 1. The glass transport cell comprises two compartments (1 and 2), with the overall glass transport cell constructed from two separate cell halves (3 and 4). The two cell halves (3 and 4) are identical cylindrical glass units. The cell halves are sealed at one end and open at the other end. Each of the cell halves comprises a magnetically controlled impeller for stirring (5 and 6) and a fill aperture (7 and 8).

The supported ionic liquid membrane (9) is positioned on the open end of one cell half. The supported ionic liquid membrane is then sandwiched between the open ends of the two cell halves (3 and 4). The two cell halves are clamped together inside a metal framework (10) in order to form a liquid-tight seal between the two compartments (1 and 2). The glass transport cell is then mounted horizontally between two mechanical stirrers bearing magnets (not shown), which are positioned to drive the magnetically controlled impellers.

The supported ionic liquid membranes used for the examples herein below are formed by the immersion of the membrane into the ionic liquid composition with which it is to be impregnated. The membrane is immersed in the ionic liquid composition until the entire membrane acquires a transparent appearance, after which the membrane is removed from the ionic liquid composition and any excess ionic liquid composition is removed from the surface of the supported ionic liquid membrane.

The separation process is performed by first charging one of the compartments of the glass transport cell with the receiving phase solvent for receiving the olefinic hydrocarbon product composition. This is designated the permeate side. The receiving phase solvent also comprises an internal standard, which is used for gas chromatography analysis of the olefinic hydrocarbon product composition. The glass transport cell is allowed to stir for 5 minutes to check for any membrane leakage. The other compartment of the glass transport cell is then charged with the feedstock composition. This is designated the feedstock side. The feedstock composition also comprises an internal standard which is used for gas chromatography analysis of the feedstock composition prior to the separation process and retentate composition after the separation process. Both compartments of the glass transport cell are allowed to stir at approximately 100 rpm for a period of 24 hours at room temperature. Samples are then taken from both the permeate side and the feedstock side after 24 hours and are analysed by gas chromatography. The gas chromatograph used is an Agilent 6850 gas chromatograph and chemstation with autosampler and flame ionisation detector. The column is a 60 m, 0.32 mm diameter, film 0.50 μm, J&W Scientific DB-1 column (all commercially available from Agilent Technologies, 395 Page Mill Rd., P.O. Box #10395, Palo Alto, Calif. 94303, USA). The temperature program of the gas chromatograph includes an initial temperature of 50° C., an initial time of 8 minutes, a rate of 10° C. min$^{-1}$ and a final temperature of 325° C. The calculation of the quantities of the components was performed using a calibrated ISTD program.

For each component of the feedstock composition, the average flux through the supported ionic liquid membrane is calculated according to the following equations:

$$J = P/A_m \times t$$

where $J$=average flux over time period t (kg m$^{-2}$ h$^{-1}$).
$P$=amount of the component in the receiving phase (permeate side), determined by gas chromatography (kg).
$A_m$=surface area of the supported ionic liquid membrane (m$^2$).
$t$=time period of the separation (h).

For comparison purposes, the flux through the supported ionic liquid membrane is normalised to 1.0 M feedstock component concentration.

The selectivity of the supported ionic liquid membrane for each olefin over its' analogous paraffin is calculated according to:

$$S = J_O/J_P$$

where
$S$=selectivity.
$J_O$=average normalised flux of the olefinic hydrocarbon.
$J_P$=average normalised flux of the analogous paraffinic hydrocarbon.

Example 1

The glass transport cell is assembled as described above. The membrane used is a polycarbonate membrane (Isopore (trade mark) membrane commercially available from Millipore, 290 Concord Rd., Billerica, Mass. 01821, USA, having an average pore diameter of 0.4 μm and a membrane thickness of 10 μm). The ionic liquid composition is a 40% mol solution of silver nitrate (commercially available from Sigma-Aldrich, 3050 Spruce St., St. Louis, Mo. 63103, USA) in 1-butyl-3-methyl-imidazolium nitrate.

The 1-butyl-3-methyl-imidazolium nitrate is synthesised by addition of an aqueous solution of silver nitrate (0.25 Mol in 100 ml water) to a stirring aqueous solution of 1-butyl-3-methyl-imidazolium chloride (commercially available from Solvent Innovation GmbH, Alarichstraβe 14-16, 50679 Köln, Germany) (0.25 Mol in 100 ml water) at room temperature and allowed to react for one hour. The silver chloride formed is removed by filtration over a glass filter (porosity: P4). The water is removed from the 1-butyl-3-methyl-imidazolium nitrate solution by evaporation. The 1butyl-3-methyl-imidazolium nitrate product is then dried in vacuo for three hours at 70° C.

The receiving phase solvent employed is tetradecane (commercially available from Sigma-Aldrich, 3050 Spruce St. St. Louis, Mo. 63103, USA) and the feedstock composition is derived from a Fischer-Tropsch synthesis, and has the composition set out in Table 1.

TABLE 1

Feedstock composition for Example 1.

| Compound | % wt. of the feedstock composition |
| --- | --- |
| 1-Pentene* | 1.4 |
| Pentane | 3.1 |
| 1-Hexene* | 5.8 |
| Hexane | 8.8 |
| 1-Heptene* | 8.8 |
| Heptane | 12.0 |
| 1-Octene* | 9.9 |
| Octane | 14.1 |
| 1-Nonene* | 11.3 |
| Nonane | 18.6 |
| 1-Decene* | 3.2 |
| Decane | 3.0 |

*contains up to 2% wt. isomeric impurities based upon the weight of each individual component.

The average flux of the compounds through the supported ionic liquid membrane over a 24 hour period is disclosed in Table 2 below.

TABLE 2

Average flux over a 24 hour period for the compounds of Example 1.

| Compound | Flux (kg/m$^2$h) |
| --- | --- |
| 1-Pentene* | 3.7 × 10$^{-02}$ |
| Pentane | 2.2 × 10$^{-03}$ |
| 1-Hexene* | 2.8 × 10$^{-02}$ |
| Hexane | 1.4 × 10$^{-03}$ |
| 1-Heptene* | 2.0 × 10$^{-02}$ |
| Heptane | 8.3 × 10$^{-04}$ |
| 1-Octene* | 1.3 × 10$^{-02}$ |
| Octane | 5.8 × 10$^{-04}$ |
| 1-Nonene* | 8.0 × 10$^{-03}$ |
| Nonane | 3.1 × 10$^{-04}$ |
| 1-Decene* | 5.3 × 10$^{-03}$ |
| Decane | 2.0 × 10$^{-03}$ |

*contains up to 2% wt. isomeric impurities based upon the weight of each individual component.

The selectivity of the supported ionic liquid membrane for olefinic hydrocarbons over their analogous paraffinic hydrocarbons over a 24 hour period is disclosed Table 3 below.

TABLE 3

Average selectivity over a 24 hour period for Example 1.

| Compounds | Selectivity |
|---|---|
| 1-Pentene*/Pentane | 16.8 |
| 1-Hexene*/Hexane | 20.0 |
| 1-Heptene*/Heptane | 24.1 |
| 1-Octene*/Octane | 22.4 |
| 1-Nonene*/Nonane | 25.8 |
| 1-Decene*/Decane | 2.7 |

*contains up to 2% wt. isomeric impurities based upon the weight of each individual component.

Example 2

The glass transport cell is assembled as described above. The membrane used is a polycarbonate membrane (Isopore (trade mark) membrane commercially available from Millipore, having an average pore diameter of 0.4 μm and a membrane thickness of 10 μm). The ionic liquid composition is a 40% mol solution of silver nitrate (commercially available from Sigma-Aldrich) in 1-butyl-3-methyl-imidazolium nitrate. The receiving phase solvent employed is heptane (commercially available from Merck KgaA, Frankfurter Str. 250, D-64293 Darmstadt, Germany) and the feedstock composition is derived from a Fischer-Tropsch synthesis, and has the composition set out in Table 4.

TABLE 4

Feedstock composition for Example 2.

| Compound | % wt. of the feedstock composition |
|---|---|
| 1-Undecene* | 11.8 |
| Undecane | 37.6 |
| 1-Dodecene* | 11.3 |
| Dodecane | 39.3 |

*contains up to 2% wt. isomeric impurities based upon the weight of each individual component.

The average flux of the compounds through the supported ionic liquid membrane over a 24 hour period is disclosed in Table 5 below.

TABLE 5

Average flux over a 24 hour period for the compounds of Example 2.

| Compound | Flux (kg/m$^2$h) |
|---|---|
| 1-Undecene* | $3.2 \times 10^{-03}$ |
| Undecane | $1.4 \times 10^{-04}$ |
| 1-Dodecene* | $1.8 \times 10^{-03}$ |
| Dodecane | $7.5 \times 10^{-05}$ |

*contains up to 2% wt. isomeric impurities based upon the weight of each individual component.

The selectivity of the supported ionic liquid membrane for olefinic hydrocarbons over their analogous paraffinic hydrocarbons over a 24 hour period is disclosed in Table 6 below.

TABLE 6

Average selectivity over a 24 hour period for Example 2.

| Compounds | Selectivity |
|---|---|
| 1-Undecene*/Undecane | 22.9 |
| 1-Dodecene*/Dodecane | 24.0 |

*contains up to 2% wt. isomeric impurities based upon the weight of each individual component.

Example 3

The glass transport cell is assembled as described above. The membrane used is a polycarbonate membrane (Isopore (trade mark) membrane commercially available from Millipore, having an average pore diameter of 0.4 μm and a membrane thickness of 10 μm). The ionic liquid composition is a 40% mol solution of silver nitrate (commercially available from Sigma-Aldrich) in 1-butyl-3-methyl-imidazolium nitrate. The receiving phase solvent employed is heptane (commercially available from Merck kgaA) and the feedstock composition is derived from a Fischer-Tropsch synthesis, and has the composition set out in Table 7.

TABLE 7

Feedstock composition for Example 3.

| Compound | % wt. of the feedstock composition |
|---|---|
| 1-Tridecene* | 9.3 |
| Tridecane | 44.8 |
| 1-Tetradecene* | 7.6 |
| Tetradecane | 38.3 |

*contains up to 2% wt. isomeric impurities based upon the weight of each individual component.

The average flux of the compounds through the supported ionic liquid membrane over a 24 hour period is disclosed in Table 8 below.

TABLE 8

Average flux over a 24 hour period for the compounds of Example 3.

| Compound | Flux (kg/m$^2$h) |
|---|---|
| 1-Tridecene* | $6.8 \times 10^{-03}$ |
| Tridecane | $6.0 \times 10^{-04}$ |
| 1-Tetradecene* | $9.0 \times 10^{-03}$ |
| Tetradecane | $4.8 \times 10^{-04}$ |

*contains up to 2% wt. isomeric impurities based upon the weight of each individual component.

The selectivity of the supported ionic liquid membrane for olefinic hydrocarbons over their analogous paraffinic hydrocarbons over a 24 hour period is disclosed in Table 9 below.

TABLE 9

Average selectivity over a 24 hour period for Example 3.

| Compounds | Selectivity |
|---|---|
| 1-Tridecene*/Tridecane | 11.3 Not changed |
| 1-Tetradecene*/Tetradecane | 18.5 Not changed |

*contains up to 2% wt. isomeric impurities based upon the weight of each individual component.

Example 4

The glass transport cell is assembled as described above. The membrane used is a polycarbonate membrane (Isopore (trade mark) membrane commercially available from Millipore, having an average pore diameter of 0.4 μm and a membrane thickness of 10 μm). The ionic liquid composition is a 40% mol solution of silver nitrate (commercially available from Sigma-Aldrich) in 1-butyl-3-methyl-imidazolium nitrate. The receiving phase solvent employed is tetradecane (commercially available from Sigma-Aldrich) and the feedstock has the composition set out in Table 10.

TABLE 10

Feedstock composition for Example 4.

| Compound | % wt. of the feedstock composition |
| --- | --- |
| 1-Hexene | 3.1 |
| Hexane | 3.2 |
| 1-Octene | 4.2 |
| Octane | 4.2 |
| 1-Decene | 5.2 |
| Decane | 5.3 |
| 1-Dodecene | 6.2 |
| Dodecane | 6.3 |
| 1-Hexadecene | 8.3 |
| Hexadecane | 8.4 |
| Heptane (internal standard) | 3.7 |
| Tetradecane (solvent) | to 100 % wt. |

The average flux of the compounds through the supported ionic liquid membrane over a 24 hour period is disclosed in Table 11 below.

TABLE 11

Average flux over a 24 hour period for the compounds of Example 4.

| Compound | Flux (kg/m$^2$h) |
| --- | --- |
| 1-Hexene | $2.6 \times 10^{-6}$ |
| Hexane | $1.3 \times 10^{-7}$ |
| 1-Octene | $1.1 \times 10^{-6}$ |
| Octane | $3.7 \times 10^{-8}$ |
| 1-Decene | $3.6 \times 10^{-7}$ |
| Decane | $1.3 \times 10^{-8}$ |
| 1-Dodecene | $1.3 \times 10^{-7}$ |
| Dodecane | $1.2 \times 10^{-8}$ |
| 1-Hexadecene | $3.1 \times 10^{-8}$ |
| Hexadecane | $2.0 \times 10^{-8}$ |

The selectivity of the supported ionic liquid membrane for olefinic hydrocarbons over their analogous paraffinic hydrocarbons over a 24 hour period is disclosed in Table 12 below.

TABLE 12

Average selectivity over a 24 hour period for Example 4.

| Compounds | Selectivity |
| --- | --- |
| 1-Hexene/Hexane | 20.0 |
| 1-Octene/Octane | 29.7 |
| 1-Decene/Decane | 27.7 |
| 1-Dodecene/Dodecane | 10.8 |
| 1-Hexadecene/Hexadecane | 1.6 |

Example 5

The glass transport cell is assembled as described above. The membrane used is a polycarbonate membrane (Isopore (trade mark) membrane commercially available from Millipore, having an average pore diameter of 0.4 μm and a membrane thickness of 10 μm). The ionic liquid composition is a 40% mol solution of silver nitrate (commercially available from Sigma-Aldrich) in 1-ethyl-3H-imidazolium nitrate (Synthesised according to: Ching K. Lee, Hsin W.Huang and Ivan J. B. Lin Chem. Commun., 2000, pages 1911-1912). The receiving phase solvent employed is tetradecane (commercially available from Sigma-Aldrich) and the feedstock has the composition set out in Table 10 above.

The average flux of the compounds through the supported ionic liquid membrane over a 24 hour period is disclosed in Table 13 below.

TABLE 13

Average flux over a 24 hour period for the compounds of Example 5.

| Compound | Flux (kg/m$^2$h) |
| --- | --- |
| 1-Hexene | $3.1 \times 10^{-6}$ |
| Hexane | $9.4 \times 10^{-8}$ |
| 1-Octene | $1.1 \times 10^{-6}$ |
| Octane | $1.6 \times 10^{-8}$ |
| 1-Decene | $3.1 \times 10^{-7}$ |
| Decane | $4.6 \times 10^{-9}$ |
| 1-Dodecene | $7.7 \times 10^{-8}$ |
| Dodecane | $9.0 \times 10^{-9}$ |
| 1-Hexadecene | $6.1 \times 10^{-9}$ |
| Hexadecane | $3.2 \times 10^{-9}$ |

The selectivity of the supported ionic liquid membrane for olefinic hydrocarbons over their analogous paraffinic hydrocarbons over a 24 hour period is disclosed in Table 14 below.

TABLE 14

Average selectivity over a 24 hour period for Example 5.

| Compounds | Selectivity |
| --- | --- |
| 1-Hexene/Hexane | 33.0 |
| 1-Octene/Octane | 68.8 |
| 1-Decene/Decane | 67.4 |
| 1-Dodecene/Dodecane | 8.6 |
| 1-Hexadecene/Hexadecane | 1.9 |

Example 6

The glass transport cell is assembled as described above. The membrane used is a polycarbonate membrane (Isopore (trade mark) membrane commercially available from Millipore, having an average pore diameter of 0.4 μm and a membrane thickness of 10 μm). The ionic liquid composition is a 20% mol solution of silver triflate (commercially available from Sigma-Aldrich) in 1-ethyl-3-methyl-imidazolium triflate (commercially available from Fluka, Industriestrasse 25, CH-9471 Buchs SG, Switzerland). The receiving phase solvent employed is tetradecane (commercially available from Sigma-Aldrich) and the feedstock has the composition set out in Table 10.

The average flux of the compounds through the supported ionic liquid membrane over a 24 hour period is disclosed in Table 15 below.

17

TABLE 15

Average flux over a 24 hour period for the compounds of Example 6.

| Compound | Flux (kg/m²h) |
| --- | --- |
| 1-Hexene | $7.8 \times 10^{-6}$ |
| Hexane | $9.5 \times 10^{-7}$ |
| 1-Octene | $4.6 \times 10^{-6}$ |
| Octane | $3.0 \times 10^{-7}$ |
| 1-Decene | $2.1 \times 10^{-6}$ |
| Decane | $1.0 \times 10^{-7}$ |
| 1-Dodecene | $8.4 \times 10^{-7}$ |
| Dodecane | $4.3 \times 10^{-8}$ |
| 1-Hexadecene | $1.1 \times 10^{-7}$ |
| Hexadecane | $5.4 \times 10^{-9}$ |

The selectivity of the supported ionic liquid membrane for olefinic hydrocarbons over their analogous paraffinic hydrocarbons over a 24 hour period is disclosed in Table 16 below.

TABLE 16

Average selectivity over a 24 hour period for Example 6.

| Compounds | Selectivity |
| --- | --- |
| 1-Hexene/Hexane | 8.2 |
| 1-Octene/Octane | 15.3 |
| 1-Decene/Decane | 21.0 |
| 1-Dodecene/Dodecane | 19.5 |
| 1-Hexadecene/Hexadecane | 20.3 |

It is evident from the above examples that the process of the present invention results in the separation of olefinic hydrocarbons from paraffinic hydrocarbons in a liquid feedstock composition comprising olefinic hydrocarbons and paraffinic hydrocarbons with a high degree of selectivity. Further, it is evident from the above examples that the process of the present invention can separate olefinic hydrocarbons in the detergent range (e.g. $C_8$-$C_{16}$) from paraffinic hydrocarbons in a liquid feedstock composition. It is also evident from the above examples that the process of the present invention can selectively separate olefinic hydrocarbons from paraffinic hydrocarbons in a liquid feedstock composition having a broad spectrum of average carbon numbers.

We claim:

1. A process for the separation of olefinic hydrocarbons from a liquid feedstock composition comprising at least one olefinic hydrocarbon and at least one paraffinic hydrocarbon, said process comprising contacting the liquid feedstock with a supported ionic liquid membrane wherein the supported ionic liquid membrane comprises a membrane impregnated with an ionic liquid composition.

2. The process of claim 1 wherein said membrane is selected from the group consisting of mesoporous and macroporous polymer membranes, ceramic membranes, zeolite membranes, and porous alumina and steel membranes.

3. The process of claim 2 wherein said membrane is selected from the group consisting of mesoporous and macroporous polymer type membrane.

4. The process of claim 1 wherein said membrane is made of a material selected from the group consisting of polyvinylidene fluoride, polyethersulfone, polyacrylate, polyetherimide, and polycarbonate.

5. The process of claim 1 wherein the ionic liquid composition comprises an ionic liquid and the ionic liquid is selected from the group consisting of liquids containing a nitrogen-containing heterocyclic or heteroaromatic cation, trialkylphosphines, thioethers, and cyclic and non-cyclic quaternary ammonium salts.

6. The process of claim 5 wherein the ionic liquid is selected from the group consisting of liquids containing a nitrogen-containing heterocyclic or heteroaromatic cation.

7. The process of claim 6 wherein the nitrogen-containing heterocyclic or heteroaromatic cation is an optionally substituted imidazolium cation.

8. The process of claim 1 wherein the ionic liquid is formed by reacting a nitrogen-containing heterocyclic ring.

9. The process of claim 8 wherein the heterocyclic ring is a heteroaromatic ring.

10. The process of claim 9 wherein the heteroaromatic ring is selected from the group consisting of optionally substituted pyridines, imidazoles, pyrroles, pyrrolidines, thiazoles, oxazoles, isooxazoles, and pyrazoles.

11. The process of claim 9 wherein the cations used in the ionic liquids are selected from the group consisting of optionally substituted imidazolium and pyridinium cations.

12. The process of claim 11 wherein imidazolium cations are used and are selected from the group consisting of those having the formula (I) below:

(I)

wherein R1, R2 and R3 are independently selected from the group consisting of hydrogen, C1-C20 alkyl groups, and C1-C20 alkoxyalkyl groups.

13. The process of claim 12 wherein R1 and R3 are independently selected from hydrogen and C1-C16 alkyl groups.

14. The process of claim 12 wherein R1 and R3 are independently selected from the group consisting of hydrogen, methyl, ethyl, propyl, butyl, hexyl, and octyl.

15. The process of claim 12 wherein R2 is hydrogen or methyl.

16. The process of claim 11 wherein pyridinium cations are used and are selected from the group consisting of those having the formula (II) below:

(II)

wherein R4 and R5 are independently selected from the group consisting of hydrogen, C1-C20 alkyl groups, and C1-C20 alkoxyalkyl groups.

17. The process of claim 16 wherein R4 and R5 are independently selected from C1-C16 alkyl groups.

18. The process of claim 16 wherein R4 and R5 are independently selected from C1-C8 alkyl groups.

19. The process of claim 16 wherein R4 and R5 are independently selected from the group consisting of methyl, ethyl, propyl, butyl, hexyl, and octyl.

20. The process of claim 1 wherein the ionic liquid composition comprises a metal salt capable of forming a complex with an olefin dissolved, dispersed, or suspended in the ionic liquid compound.

21. The process of claim 1 wherein the liquid feedstock composition comprises at least one olefinic hydrocarbon which contains from 6 to 18 carbon atoms.

22. The process of claim 1 wherein the liquid feedstock composition is derived from a Fischer-Tropsch process.

23. The product of the process of claim 1 wherein an olefinic hydrocarbon product composition is produced and the amount of paraffinic hydrocarbons in the olefinic hydrocarbon product composition is less than about 20% wt.

* * * * *